United States Patent [19]

Chang

[11] Patent Number: 4,692,182
[45] Date of Patent: * Sep. 8, 1987

[54] HERBICIDAL ISOXAZOLIDINONE DERIVATIVES

[75] Inventor: Jun H. Chang, Princeton Junction, N.J.

[73] Assignee: FMC Corporation, Philadelphia, Pa.

[*] Notice: The portion of the term of this patent subsequent to Nov. 12, 2002 has been disclaimed.

[21] Appl. No.: 864,686

[22] Filed: May 19, 1986

[51] Int. Cl.$^4$ .................. A01N 43/80; C07D 261/04
[52] U.S. Cl. ........................................ 71/88; 548/243
[58] Field of Search .................... 548/243; 71/88, 121

[56] References Cited

U.S. PATENT DOCUMENTS

| | | | |
|---|---|---|---|
| 4,202,839 | 5/1980 | Hunter et al. | 71/88 |
| 4,404,402 | 9/1983 | Ladner et al. | 564/442 |
| 4,405,357 | 9/1983 | Chang | 71/88 |
| 4,465,508 | 8/1984 | Barton et al. | 71/103 |
| 4,552,585 | 11/1985 | Chang | 71/88 |

OTHER PUBLICATIONS

Chemical and Engineering News, Jul. 7, 1986, pp. 7–8.
Chemical Abstracts, vol. 96, (1982), 34827x.
Org. Syn., Coll. Vol. I, 240, (1941).
Org. Syn., Coll. Vol. IV, 74, (1963).
H. Zollinger, "Diazo and Azo Chemistry," Interscience Publishers, Inc., New York, N.Y., 1961, p. 169.
Nelsen, et al., Tetrahedron Letters, 2321, (1973).

Primary Examiner—Donald G. Daus
Assistant Examiner—Barbara Cassatt
Attorney, Agent, or Firm—Richard L. Hansen; William Schmonsees; H. Robinson Ertelt

[57] ABSTRACT

Isoxazolidinones of the following formula are herbicides:

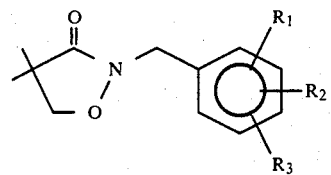

or an agriculturally acceptable salt thereof in which $R_1$ and $R_2$ are independently selected from -hydrogen and -halogen; and $R_3$ is of the formula

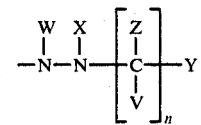

wherein
n is 0 or 1, and
when n is 0,
W is selected from -hydrogen, -lower alkyl, -lower haloalkanoyl, and -benzoyl;
X is selected from -hydrogen and -lower alkyl; and
Y is selected from -hydrogen, -lower alkyl, -cycloalkyl, -lower alkanoyl, -lower haloalkanoyl, -benzoyl, -2-nitro-5-(2-chloro-4-trifluoromethylphenoxy)benzoyl, -2,4-dichlorophenoxyacetyl, -lower alkyloxycarbonyl, -lower alkyloxycarbonyl, -lower alkylaminocarbonyl, -phenylaminocarbonyl, and -lower alkylthiocarbonyl; or
W and X together constitute a chemical bond; and Y is selected from -nitrogen and -lower alkyloxycarbonyl; and
when n is 1,
X and Z together constitute a chemical bond;
W is -hydrogen;
V is selected from -hydrogen and -lower alkyl; and
Y is selected from -lower alkyl, -phenyl, -carboxyl, and -lower alkyloxycarbonyl, or
V and Y together are an alkyl chain of 4–6 carbon atoms.

18 Claims, No Drawings

HERBICIDAL ISOXAZOLIDINONE DERIVATIVES

This invention relates to heterocyclic organic chemical compounds which contain an isoxazolidinone nucleus and exhibit herbicidal activity. More specifically, the herbicidal compounds, agricultural compositions, and method of use of this invention utilize 2-[(substituted phenyl)methyl]-4,4-dimethyl-3-isoxazolidinones as the active ingredient.

U.S. Pat. Nos. 4,405,357 and 4,552,585 describe 2-[(substituted phenyl)methyl]-4,4-dimethyl-3-isoxazolidinones in which the substituents on the 2-phenylmethyl group includes hydrogen, halogen, alkyl, phenyl, haloalkyl, nitro, alkoxy, methylenedioxy, cyano, and amido. The herbicidal 2-[(substituted phenyl)methyl]-4,4-dimethyl-3-isoxazolidinones of the present invention are represented by the following structural formula

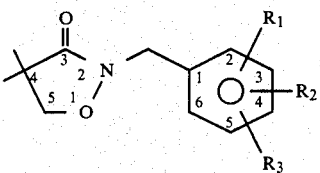

or an agriculturally acceptable salt thereof in which $R_1$ and $R_2$ independently selected from -hydrogen and -halogen; and $R_3$ is of the formula

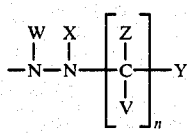

wherein
n is 0 or 1, and
when n is 0,
W is selected from -hydrogen, -lower alkyl, -lower haloalkanoyl, and -benzoyl;
X is selected from -hydrogen and -lower alkyl; and
Y is selected from -hydrogen, -lower alkyl, -cycloalkyl, -lower alkanoyl, -lower haloalkanoyl, -benzoyl, -2-nitro-5-(2-chloro-4-trifluoromethylphenoxy)benzoyl, -2,4-dichlorophenoxyacetyl, -lower alkyloxycarbonyl, -lower alkylaminocarbonyl, -phenylaminocarbonyl, and -lower alkylthiocarbonyl; or
W and X together constitute a chemical bond; and Y is selected from -nitrogen and -lower alkyloxycarbonyl; and
when n is 1,
X and Z together constitute a chemical bond;
W is -hydrogen;
V is selected from -hydrogen and -lower alkyl; and
Y is selected from -lower alkyl, -phenyl, -carboxyl, and -lower alkyloxycarbonyl, or
V and Y together are an alkyl chain of 4-6 carbon atoms.

In the aforesaid description and wherever the terms appear hereinafter, "halo" and "halogen" mean fluorine, chlorine or bromine. The term "lower" modifying "alkyl," "alkanoyl;." "alkyloxycarbonyl," "alkylaminocarbonyl," "alkylthiocarbonyl," and the like, implies a straight or branched hydrocarbon chain of 1-6, preferably 1-4, carbon atoms; "halo" coupled with another term means one or more hydrogen atoms has been replaced by halogen. The term "cycloalkyl" means a saturated ring containing 3-8 carbon atoms.

Among the aforesaid compounds it is preferred that $R_1$ be a 2-chloro substituent and that $R_2$ be hydrogen. With regard to $R_3$, W is hydrogen in the most active compounds, while X is either hydrogen or X and Z together constitute a chemical bond.

The 2-[(substituted phenyl)methyl]-4,4-dimethyl-3-isoxazolidinones of this invention are prepared from 2-[(aminophenyl)methyl]-4,4-dimethyl-3-isoxazolidinones carrying the desired $R_1$ and $R_2$ substituents. These 2-[(aminophenyl)methyl]-4,4-dimethyl-3-isoxazolidinones, in turn, are available by methods described in U.S. Pat. Nos. 4,552,585; 4,405,357; and 4,465,508, as well as Org. Syn., Coll. Vol. I, 240 (1941).

The 2-[(aminophenyl)methyl]-4,4-dimethyl-3-isoxazolidinones carrying appropriate $R_1$ and $R_2$ substituents are converted into the herbicidal isoxazolidinones of this invention by various techniques disclosed in the technical literature. For example, the amino group can be converted to azido by the procedure described in Org. Syn., Coll. Vol. IV, 74 (1963). The amino group is converted to hydrazino by the procedures described in H. Zollinger, "Diazo and Azo Chemistry," Interscience Publishers Inc., New York, New York, 1961, page 169. The hydrazino group can be alkylated by the process described in Tetrahedron Letters, 2321 (1973). The hydrazides result by treating the hydrazino compound with an acyl halide, while treatment with an aldehyde or ketone yields the semicarbazone. The hydrazine carboxylic acid esters are prepared by treating the corresponding hydrazine compounds with haloformic acid esters or appropriately substituted isocyanates.

The preparation of herbicidal isoxazolidinones within the scope of this invention is more specifically illustrated by the following examples. Additional specific examples are set forth in Table 1.

EXAMPLE 2

2-[(2-Chloro-6-hydrazinophenyl)methyl]-4,4-dimethyl-3-isoxazolidinone

A mixture of 2-chloro-6-nitrobenzyl bromide (17.5 g, 0.07 mole), 4,4-dimethyl-3-isoxazolidinone (11.5 g, 0.1 mole), potassium carbonate (13.8 g, 0.1 mole), and 1,4,7,10,13,16-hexaoxacyclooctadecane (0.5 g, 0.002 mole) in acetonitrile (500 ml) was stirred at ambient temperature overnight. The reaction mixture was poured into ethyl acetate (500 ml) and the mixture washed with water (3×200 ml). The dried (magnesium sulfate) ethyl acetate layer was concentrated under reduced pressure to yield a liquid. The liquid product was subjected to chromatography on silica gel, eluting with 1:9 ethyl acetate:heptane. The appropriate fractions were combined and concentrated under reduced pressure to yield a white solid. The solid was recrystallized from ethyl acetate to yield 10.5 g of 2-[(2-chloro-6-nitrophenyl)methyl]-4,4-dimethyl-3-isoxazolidinone, m.p. 86°–88° C.

Under an argon atmosphere, platinum oxide (0.3 g) was added to a Parr bottle (500 ml), followed by a solution of 2-[(2-chloro-6-nitrophenyl)methyl]-4,4-dimethyl-3-isoxazolidinone (9.4 g, 0.033 mole) in ethanol (150 ml). The Parr bottle was placed on a Parr hydrogenation apparatus and charged with hydrogen. The reaction mixture was allowed to shake until the calculated amount of hydrogen was absorbed. The catalyst was removed by vacuum filtration. The filtrate was concentrated under reduced pressure to a residue. The residue was chromatographed on silica gel, eluting with 1:4 ethyl acetate:heptane. The appropriate fractions were combined and concentrated under reduced pressure to yield 5.0 g of 2-[(6-amino-2-chlorophenyl)methyl]-4,4-dimethyl-3-isoxazolidinone as a white solid.

To a stirred solution of concentrated hydrochloric acid (50 ml) was added 2-[(6-amino-2-chlorophenyl)methyl]-4,4-dimethyl-3-isoxazolidinone (4.9 g, 0.019 mole). The reaction mixture was cooled to 0° C., and a solution of sodium nitrite (1.3 g, 0.019 mole) in water (20 ml) was added dropwise, with the tip of the addition funnel below the surface of solution. Upon completion of addition, the reaction mixture was stirred at 0° C. for 30 minutes. A solution of stannous chloride dihydrate (9.5 g, 0.042 mole) in concentrated hydrochloric acid (30 ml) was then added dropwise. Upon completion of addition, the reaction mixture was stirred at 0° C. for one hour, after which time an insoluble material was removed by filtration. Ethyl acetate was added to the filtrate and more insoluble material was removed. The ethyl acetate mixture was concentrated under reduced pressure, made basic with aqueous sodium hydroxide, and extracted with methylene chloride. The methylene chloride extract was concentrated under reduced pressure. Concentrated hydrochloric acid was added to the residue and the mixture was concentrated under reduced pressure to yield 1.8 g of 2-[(2-chloro-6-hydrazinophenyl)methyl]-4,4-dimethyl-3-isoxazolidinone hydrochloride as a yellow solid; m.p. 180°–184° C. (dec). The NMR spectrum was consistent with the proposed structure.

The free hydrazine was obtained by treating of the yellow solid with aqueous sodium hydroxide. The mixture was extracted with ethyl acetate, and the extract was concentrated under reduced pressure to yield the free hydrazine.

EXAMPLE 17

2-[[2-Chloro-4-(2,2-diethylhydrazinyl)phenyl]methyl]-4,4-dimethyl-3-isoxazolidinone Acetaldehyde (0.3 ml, 0.007 mole) was added by pipet to a stirred solution of 2-[(2-chloro-4-hydrazinophenyl)methyl]-4,4-dimethyl-3-isoxazolidinone hydrochloride (0.8 g, 0.0026 mole) and sodium cyanoborohydride (0.16 g, 0.0026 mole), in acetonitrile 25 ml). Glacial acetic acid (2 ml) was added, and the resulting mixture stirred at ambient temperature overnight. The reaction mixture was diluted with ether (200 ml) and washed with aqueous 0.5N sodium hydroxide (50 ml), then with water (2×50 ml). The ether layer was dried and then concentrated under reduced pressure to yield a yellow oil. The oil was chromatographed on silica gel, eluting with 30:70 ethyl acetate:heptane. Appropriate fractions were combined and concentrated under reduced pressure to yield 0.24 g of 2-[[2-chloro-4-(2,2-diethylhydrazinyl)phenyl]methyl]-4,4-dimethyl-3-isoxazolidinone as a white solid; m.p. 139°–141° C. The NMR spectrum was consistent with the proposed structure.

EXAMPLE 19

2-[[2-Chloro-5-(methylcarbonylhydrazo)phenyl]methyl]-4,4-dimethyl-3-isoxazolidinone Triethylamine (0.6 g, 0.0055 mole) was added to a stirred solution of 2-[(2-chloro-5-hydrazinophenyl)methyl]-4,4-dimethyl-3-isoxazolidinone hydrochloride (1.5 g, 0.005 mole) in methylene chloride (50 ml), followed by the dropwise addition of acetic anhydride (0.6 g, 0.0055 mole). Upon completion of addition, the reaction mixture was stirred at ambient temperature overnight. The reaction mixture was diluted with ethyl acetate (200 ml) and washed with water (3×50 ml). The dried (magnesium sulfate) organic layer was concentrated under reduced pressure. The residue was recrystallized from ethanol-water to yield 0.95 g of 2-[[2-chloro-5-(methylcarbonylhydrazo)phenyl]methyl]-4,4-dimethyl-3-isoxazolidinone as a yellow solid; m.p. 178°–180° C. The NMR spectrum was consistent with the proposed structure.

EXAMPLE 34

2-[[2-Chloro-4-[(2,4-dichlorophenoxy)methylcarbonylhydrazo]phenyl]methyl-4,4-dimethyl-3-isoxazolidinone A mixture of 2,4-dichlorophenoxyacetic acid (5.0 g, 0.023 mole) and thionyl chloride (3.0 ml, 0.029 mole) in toluene (100 ml) was heated at reflux for two hours. Upon cooling, the reaction mixture was concentrated under reduced pressure to remove most of the solvent. The residual 2,4-dichlorophenoxyacetyl chloride was used without further purification in the following reaction.

A stirred solution of 2-[(2-chloro-4-hydrazinophenyl)methyl]-4,4-dimethyl-3-isoxazolidinone hydrochloride (1.5 g, 0.0049 mole) and triethylamine (1.4 ml) in tetrahydrofuran (100 ml) was cooled to 10° C. and 2,4-dichlorophenoxyacetyl chloride (0.80 g, 0.0067 mole) was added in one portion. The reaction mixture was stirred overnight at ambient temperature. Triethylamine hydrochloride was removed by filtration, and the filtrate concentrated under reduced pressure. The residue was chromatographed on silica gel, eluting with 60:40 ethyl acetate:heptane. Appropriate fractions were combined and concentrated under reduced pressure. The residual solid was recrystallized from ethyl acetate:heptane to yield 2-[[2-chloro-4-[(2,4-dichlorophenoxy)methylcarbonylhydrazo]phenyl]methyl]-4,4-dimethyl-3-isoaolidinone as a yellow solid; m.p. 149°–150° C. The NMR spectrum was consistent with the proposed structure.

EXAMPLE 45

2-[[2-Chloro-4-(2-ethylidenyl-1-hydrazinyl)-phenyl]methyl]-4,4-dimethyl-3-isoxazolidinone Acetaldehyde, in large excess, was added via pipet to a stirred solution of 2-[(2-chloro-4-hydrazino phenyl)-methyl]-4,4-dimethyl-3-isoxazolidinone hydrochloride (0.7 g, 0.00229 mole) in water (40 ml). The reaction mixture was stirred for 20 minutes at ambient temperature. A white solid was removed by filtration to yield 2-[[2-chloro-4-(-ethylidenyl-1-hydrazinyl)phenyl]methyl]-4,4-dimethyl-3-isoxazolidinone; m.p. 167°–169° C. The NMR spectrum was consistent with the proposed structure.

EXAMPLE 71

2-[[2-Chloro-4-(ethoxycarbonylazo)phenyl]methyl]-4,4-dimethyl-3-isoxazolidinone

A stirred mixture of 2-[[2-chloro-4-(ethoxycarbonylhydrazo)phenyl]methyl]-4,4-dimethyl-3-isoxazolidinone (1.24 g, 0.0036 mole) and magnesium sulfate (0.5 g, 0.004 mole) in toluene was cooled in a water bath. Silver oxide (0.6 g) was added and the mixture was stirred for one hour. Additional silver oxide (0.6 g) was added, and the mixture was stirred an additional one hour. The reaction mixture was filtered and the filtrate concentrated under reduced pressure. The residue was chromatographed on silica gel, eluting first with 1:4 ethyl acetate:heptane and then 1:1 ethyl acetate:heptane. Appropriate fractions were combined and concentrated under reduced pressure to yield 1.0 g of 2-[[2-chloro-4-(ethoxycarbonylazo)phenyl]methyl]-4,4-dimethyl-3-isoxazolidinone as a red oil. The NMR spectrum was consistent with the proposed structure.

EXAMPLE 72

2-[(3-Azido-2-chlorophenyl)methyl]-4,4-dimethyl-3-isoxazolidinone

Concentrated hydrochloric acid (25 ml) was added dropwise to a stirred mixture of 2-[(3-amino-2-chlorophenyl)methyl]-4,4-dimethyl-3-isoxazolidinone (6.45 g, 0.025 mole) and water (75 ml). The reaction mixture was cooled to 0° C., and a solution of sodium nitrite (2.0 g, 0.03 moles) in water (25 ml) was added dropwise. Upon completion of addition, the reaction mixture was stirred at 0° C. for 30 minutes. An insoluble material was removed by filtration. The filtrate was cooled to 0° C., and sodium azide (1.6 g, 0.025 mole) was added portionwise. Upon completion of addition, the reaction mixture was stirred for 15 minutes. The reaction mixture was diluted with water (500 ml) and extracted with methylene chloride (3×100 ml). The dried (sodium sulfate) methylene chloride extract was concentrated under reduced pressure to yield 5.3 g of 2-[(3-azido-2-chlorophenyl)methyl]-4,4-dimethyl-3-isoxazolidinone as a brown oil. The NMR spectrum was consistent with the proposed structure.

TABLE 1

| Ex. | Additional Examples |
|---|---|
| 1 | 2-[(2-Hydrazinophenyl)methyl]-4,4-dimethyl-3-isoxazolidinone hydrochloride. |
| 3 | 2-[(2-Chloro-3-hydrazinophenyl)methyl]-4,4-dimethyl-3-isoxazolidinone hydrochloride, mp 198–202° C. dec. |
| 4 | 2-[(2-Fluoro-4-hydrazinophenyl)methyl]-4,4-dimethyl-3-isoxazolidinone, mp 78° C. dec. |
| 5 | 2-[(2-Fluoro-4-hydrazinophenyl)methyl]-4,4-dimethyl-3-isoxazolidinone hydrochloride, mp 202° C. dec. |
| 6 | 2-[(2-Chloro-4-hydrazinophenyl)methyl]-4,4-dimethyl-3-isoxazolidinone, mp 93–96° C. |
| 7 | 2-[(2-Chloro-4-hydrazinophenyl)methyl]-4,4-dimethyl-3-isoxazolidinone hydrochloride, mp 206–209° C. dec. |
| 8 | 2-[(2-Bromo-4-hydrazinophenyl)methyl]-4,4-dimethyl-3-isoxazolidinone, mp 102° C. dec. |
| 9 | 2-[(2-Bromo-4-hydrazinophenyl)methyl]-4,4-dimethyl-3-isoxazolidinone hydrochloride, mp 180° C. dec. |
| 10 | 2-[(2,5-Dichloro-4-hydrazinophenyl)methyl]-4,4-dimethyl-3-isoxazolidinone hydrochloride, mp 208–210° C. |
| 11 | 2-[(2-Chloro-5-hydrazinophenyl)methyl]-4,4-dimethyl-3-isoxazolidinone, mp 98–100° C. |
| 12 | 2-[(2-Chloro-5-hydrazinophenyl)methyl]-4,4-dimethyl-3-isoxazolidinone hydrochloride, mp 198–202° C. |
| 13 | 2-[(2-Chloro-4-fluoro-5-hydrazinophenyl)methyl]-4,4-dimethyl-3-isoxazolidinone, mp 78–80° C. |
| 14 | 2-[(2-Chloro-4-fluoro-5-hydrazinophenyl)methyl]-4,4-dimethyl-3-isoxazolidinone hydrochloride, mp 150° C. dec. |
| 15 | 2-[(2,4-Dichloro-5-hydrazinophenyl)methyl]-4,4-dimethyl-3-isoxazolidinone, mp 96–98° C. |
| 16 | 2-[(2,4-Dichloro-5-hydrazinophenyl)methyl]-4,4-dimethyl-3-isoxazolidinone hydrochloride, mp 203–207° C. |
| 18 | 2-[[2-Chloro-4-(2,2-dipropylhydrazinyl)phenyl]methyl]-4,4-dimethyl-3-isoxazolidinone, mp 94–96° C. |
| 20 | 2-[[2,4-Dichloro-5-(methylcarbonylhydrazo)phenyl]methyl]4,4-dimethyl-3-isoxazolidinone, mp 128–130° C. |
| 21 | 2-[[2-Fluoro-4-(methylcarbonylhydrazo)phenyl]methyl]-4,4-dimethyl-3-isoxazolidinone, mp 202° C. |
| 22 | 2-[[2-Chloro-4-(methylcarbonylhydrazo)phenyl]methyl]-4,4-dimethyl-3-isoxazolidinone, mp 205–209° C. |
| 23 | 2-[[2-Bromo-4-(methylcarbonylhydrazo)phenyl]methyl]-4,4-dimethyl-3-isoxazolidinone, mp 190–192° C. |
| 24 | 2-[[2-Chloro-4-(ethylcarbonylhydrazo)phenyl]methyl]-4,4-dimethyl-3-isoxazolidinone, mp 178–179° C. |
| 25 | 2-[[2-Chloro-4-(propylcarbonylhydrazo)phenyl]methyl]-4,4-dimethyl-3-isoxazolidinone, mp 156–158° C. |
| 26 | 2-[[2-Chloro-4-(butylcarbonylhydrazo)phenyl]methyl]-4,4-dimethyl-3-isoxazolidinone, mp 117–119° C. |
| 27 | 2-[[2-Chloro-4-[(1-methylethyl)carbonylhydrazo]phenyl]methyl]-4,4-dimethyl-3-isoxazolidinone, mp 181–182° C. |
| 28 | 2-[[2-Chloro-4-[(1,1-dimethylethyl)carbonylhydrazo]phenyl]methyl]-4,4-dimethyl-3-isoxazolidinone, mp 186–187° C. |
| 29 | 2-[[2-Chloro-4-(cyclopropylcarbonylhydrazo)phenyl]methyl]-4,4-dimethyl-3-isoxazolidinone, mp 187–192° C. |
| 30 | 2-[[2-Chloro-5-(chloromethylcarbonylhydrazo)phenyl]methyl]-4,4-dimethyl-3-isoxazolidinone, mp 156–157° C. |
| 31 | 2-[[2-Chloro-4-(chloromethylcarbonylhydrazo)phenyl]methyl]-4,4-dimethyl-3-isoxazolidinone, mp 169–170° C. |
| 32 | 2-[[2-Chloro-5-(phenylcarbonylhydrazo)phenyl]methyl]-4,4-dimethyl-3-isoxazolidinone, mp 154–155° C. |
| 33 | 2-[[2-Chloro-4-(phenylcarbonylhydrazo)phenyl]methyl]-4,4-dimethyl-3-isoxazolidinone, mp 175–177° C. |
| 35 | 2-[[2-Chloro-4-[2-nitro-5-(2-chloro-4-trifluoromethylphenoxy)phenylcarbonylhydrazo]phenyl]methyl]-4,4-dimethyl-3-isoxazolidinone. |
| 36 | 2-[[2-Chloro-4-fluoro-5-[2-nitro-5-(2-chloro-4-trifluoromethylphenoxy)phenylcarbonylhydrazo]phenyl]methyl]-4,4-dimethyl-3-isoxazolidinone, mp 85° C. dec. |
| 37 | 2-[[2-Chloro-5-(ethoxycarbonylhydrazo)phenyl]methyl]-4,4-dimethyl-3-isoxazolidinone, mp 139–140° C. |
| 38 | 2-[[2-Chloro-4-(ethoxycarbonylhydrazo)phenyl]methyl]-4,4-dimethyl-3-isoxazolidinone, mp 98–101° C. |
| 39 | 2-[[2-Chloro-4-(methylaminocarbonylhydrazo)phenyl]methyl]-4,4-dimethyl-3-isoxazolidinone, mp 183–186° C. |
| 40 | 2-[[2-Chloro-4-(phenylaminocarbonylhydrazo)phenyl]methyl]-4,4-dimethyl-3-isoxazolidinone, mp 158–160° C. |
| 41 | 2-[[2-Chloro-4-(ethylthiocarbonylhydrazo)phenyl]methyl]-4,4-dimethyl-3-isoxazolidinone, mp 162–164° C. |
| 42 | 2-[[2-Chloro-4-(1,2,2-trimethylhydrazinyl)phenyl]methyl]-4,4-dimethyl-3-isoxazolidinone, mp 91–95° C. |
| 43 | 2-[[2-Chloro-5-[1,2-di(chloromethylcarbonyl)hydrazinyl]phenyl]methyl]-4,4-dimethyl-3-isoxazolidinone. |
| 44 | 2-[[2-Chloro-5-[1,2-di(phenylcarbonyl)hydrazinyl]phenyl]methyl]-4,4-dimethyl-3-isoxazoli- |

TABLE 1-continued
Additional Examples

| Ex. | |
|---|---|
| | dinone, mp 158–159° C. |
| 46 | 2-[[2-Chloro-4-(2-propylidenyl-1-hydrazinyl)-phenyl]methyl]-4,4-dimethyl-3-isoxazolidinone, mp 153–157° C. |
| 47 | 2-[[2-Chloro-4-[2-(1-methylethylidenyl)-1-hydrazinyl]phenyl]methyl]-4,4-dimethyl-3-isoxazolidinone, mp 158–160° C. |
| 48 | 2-[[2,4-Dichloro-5-[2-(1-methylethylidenyl)-1-hydrazinyl]phenyl]methyl]-4,4-dimethyl-3-isoxazolidinone, mp 74–76° C. |
| 49 | 2-[[2-Fluoro-4-[2-(1-ethylpropylidenyl)-1-hydrazinyl]phenyl]methyl]-4,4-dimethyl-3-isoxazolidinone, mp 135° C. dec. |
| 50 | 2-[[2-Chloro-4-[2-(1-ethylpropylidenyl)-1-hydrazinyl]phenyl]methyl]-4,4-dimethyl-3-isoxazolidinone, mp 101–107° C. |
| 51 | 2-[[2-Chloro-4-[2-(2,2-dimethylpropylidenyl)-1-hydrazinyl]phenyl]methyl]-4,4-dimethyl-3-isoxazolidinone. |
| 52 | 2-[[2-Chloro-6-(2-cyclohexylidenyl-1-hydrazinyl)phenyl]methyl]-4,4-dimethyl-3-isoxazolidinone, mp 118–121° C. |
| 53 | 2-[[2-Fluoro-4-(2-cyclohexylidenyl-1-hydrazinyl)phenyl]methyl]-4,4-dimethyl-3-isoxazolidinone, mp 152° C. |
| 54 | 2-[[2-Chloro-4-(2-cyclohexylidenyl-1-hydrazinyl)phenyl]methyl]-4,4-dimethyl-3-isoxazolidinone, mp 131–140° C. dec. |
| 55 | 2-[[2-Bromo-4-(2-cyclohexylidenyl-1-hydrazinyl)phenyl]methyl]-4,4-dimethyl-3-isoxazolidinone, mp 158–159° C. |
| 56 | 2-[[2,5-Dichloro-4-(2-cyclohexylidenyl-1-hydrazinyl)phenyl]methyl]-4,4-dimethyl-3-isoxazolidinone, mp 98–101° C. |
| 57 | 2-[[2-Chloro-4-(2-benzylidenyl-1-hydrazinyl)phenyl]methyl]-4,4-dimethyl-3-isoxazolidinone, mp 190–195° C. |
| 58 | 2-[[2-Chloro-4-[2-(1-phenylethylidenyl)-1-hydrazinyl]phenyl]methyl]-4,4-dimethyl-3-isoxazolidinone, mp 159–160° C. |
| 59 | 2-[[2-Chloro-5-[2-(1-carboxyethylidenyl)-1-hydrazinyl]phenyl]methyl]-4,4-dimethyl-3-isoxazolidinone, mp 168–170° C. |
| 60 | 2-[[4-Chloro-2-fluoro-5-[2-(1-carboxyethylidenyl)-1-hydrazinyl]phenyl]methyl]-4,4-dimethyl-3-isoxazolidinone hydrate, mp 105–110° C. |
| 61 | 2-[[2-Chloro-4-fluoro-5-[2-(1-carboxyethylidenyl)-1-hydrazinyl]phenyl]methyl]-4,4-dimethyl-3-isoxazolidinone hydrate, mp 124° C. dec. |
| 62 | 2-[[2,4-Dichloro-5-[2-(1-carboxyethylidenyl)-1-hydrazinyl]phenyl]methyl]-4,4-dimethyl-3-isoxazolidinone, mp 140–143° C. |
| 63 | 2-[[2-Fluoro-4-[2-(1-carboxyethylidenyl)-1-hydrazinyl]phenyl]methyl]-4,4-dimethyl-3-isoxazolidinone, mp 215° C. dec. |
| 64 | 2-[[2-Chloro-4-[2-(1-carboxyethylidenyl)-1-hydrazinyl]phenyl]methyl]-4,4-dimethyl-3-isoxazolidinone, mp 202–204°0 C. |
| 65 | 2-[[2-Bromo-4-[2-(1-carboxyethylidenyl)-1-hydrazinyl]phenyl]methyl]-4,4-dimethyl-3-isoxazolidinone, mp 175° C. dec. |
| 66 | 2-[[2,5-Dichloro-4-[2-(1-carboxyethylidenyl)-1-hydrazinyl]phenyl]methyl]-4,4-dimethyl-3-isoxazolidinone, mp 84–87° C. |
| 67 | 2-[[2-Chloro-5-[2-(1-ethoxycarbonylethylidenyl)-1-hydrazinyl]phenyl]methyl]-4,4-dimethyl-3-isoxazolidinone, mp 140–143° C. |
| 68 | 2-[[2-Fluoro-4-[2-(1-ethoxycarbonylethylidenyl)-1-hydrazinyl]phenyl]methyl]-4,4-dimethyl-3-isoxazolidinone, mp 125–128° C. |
| 69 | 2-[[2-Chloro-4-[2-(1-ethoxycarbonylethylidenyl)-1-hydrazinyl]phenyl]methyl]-4,4-dimethyl-3-isoxazolidinone, mp 145–147° C. |
| 70 | 2-[[2-Bromo-4-[2-(1-ethoxycarbonylethylidenyl)-1-hydrazinyl]phenyl]methyl]-4,4-dimethyl-3-isoxazolidinone, mp 149–150° C. |
| 73 | 2-[(5-Azido-2-chlorophenyl)methyl]-4,4-dimethyl-3-isoxazolidinone, mp 83–85° C. |
| 74 | 2-[(4-Azido-2-chlorophenyl)methyl]-4,4-di- |

TABLE 1-continued
Additional Examples

| Ex. | |
|---|---|
| | methyl-3-isoxazolidinone, mp 63–65° C. |

In the normal use of the aforesaid 2-[(substituted phenyl)methyl]-4,4-dimethyl-3-isoxazolidinone herbicides, the active compounds usually will not be employed free from admixture or dilution, but ordinarily will be used in a suitable formulated agricultural composition compatible with the method of application and comprising a herbicidally effective amount of at least one of said active isoxazolidinones. Said isoxazolidinones, like most pesticidal agents, may be blended with the agriculturally acceptable surface-active agents and carriers normally employed for facilitating the dispersion of active ingredients, recognizing the accepted fact that the formulation and mode of application of a herbicide may affect the activity of the material. The present active isoxazolidinones may be applied, for example, as sprays, dusts, or granules to the area where plant growth control is desired, the type of application varying, of course, with the plant and the environment. Thus, the isoxazolidinones of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said active compounds. The granule particles are relatively large, a diameter of about 400–2500 microns typically. The particles are either impregnated with the active compound from solution or coated with the compound, adhesive sometimes being employed. Granules generally contain 0.05–20% by weight, preferably 0.5–5%, active ingredient as the herbicidally effective amount. A typical granular formulation employed for evaluation purposes contains 95% attapulgite clay (24/48 mesh) and 5% 2-[(2-chloro-6-hydrazinophenyl)methyl]-4,4-dimethyl-3-isoxazolidinone.

Dusts are admixtures of said active compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the herbicide. These finely divided solids have an average particle size of less than about 50 microns. A typical dust formulation useful for controlling plant growth contains by weight 5 parts 2-[[2-chloro-4-(2-ethylidenyl-1-hydrazinyl)phenyl]methyl]-4,4-dimethyl-3-isoxazolidinone and 95 parts talc.

The isoxazolidinones of the present invention may be made into liquid concentrates by dissolution or emulsification in suitable liquids and into solid concentrates by admixture with talc, clays, and other known solid carriers used in the pesticide art. The concentrates are compositions containing, as a herbicidally effective amount, about 5–50% the isoxazolidinone by weight and 95–50% inert material, which includes surface-active dispersing, emulsifying and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the solid products together with one percent or more of a solvent to produce a concentrate which does not solidify on cooling to the freezing point or below of the pure product.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the herbicidal composition.

Other useful formulations include simple solutions of the active ingredient in a solvent which it is completely soluble at the desired concentration, such as acetone or other organic solvents.

A herbicidally effective amount of said herbicidal isoxazolidinone in a herbicidal composition diluted for application is normally in the range of about 0.004% to about 5% by weight. Many variations of spraying and dusting compositions known in the art may be used by substituting said herbicidal isoxazolidinones of this invention into compositions known or apparent to the art. The herbicidal compositions of this invention may be formulated with other active ingredients, including insecticides, nematicides, acaricides, fungicides, plant growth regulators, fertilizers, etc.

In using the compositions to control plant growth according to the method of this invention, it is only necessary that a herbicidally effective amount of at least one of said herbicidal isoxazolidinones be applied to the locus where control is desired, generally a soil locus where agricultural crops are grown and either before or after the plants have emerged. Liquid herbicidal compositions may be incorporated into the soil, applied to the soil as a drench, or sprayed on the foliage of growing plants. Solid compositions may be applied by broadcasting or in bands. For most applications, a herbicidally effective amount will be about 0.1 to 8 kg, preferably 0.1 to 2 kg, per hectare.

The herbicidal isoxazolidinones of this invention were investigated for activity in preemergence and postemergence tests according to the following procedure:

Flats were filled with a steam-sterilized sandy loam soil. Seeds of the following test plant species were planted in furrows: cotton (*Gosssypium hirsutum*) or lima bean (*Phaseolus limensis*), field corn (*Zea mays L.*), soybean (*Glycine max*), wheat (*Triticum aestivum*), barnyardgrass (*Echinochloa crus galli*), johnsongrass (*Sorghum halepense*), pitted morningingglory (*Ipomoea lacunosa*), velvetleaf (*Abutilon theophriasti*), field bindweed (*Convolvulus arvenia*), Bermuda grass (*Cynodon dactylon*), yellow nutsedge (*Cyperus esculentus*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for preemergence test was watered and the soil evenly drenched with the water-acetone solution of test chemical. The treated flat was placed in a greenhouse where it was watered regularly at the soil surface for a period of 13 days. The effect of the test chemical was then recorded. In some tests individual plant species were examined for percent kill and a vigor rating of one to five was assigned to the surviving plants, a vigor of five signifying no chemical injury. In other tests percent kill and vigor rating were combined in a single rating called "percent control," which has the following significance:

| Percent Control | Description of Effect | Effect on Crops | Effect on Weeds |
|---|---|---|---|
| 0 | No effect | No crop reduction | No weed control |
| 10 |  | Slight discoloration or stunting | Very poor weed control |
| 20 | Slight effect | Some discoloration, stunting or stand loss | Poor weed control |
| 30 |  | Crop injury more pronounced but not lasting | Poor to deficient weed control |
| 40 |  | Moderate injury, crop usually recovers | Deficient weed control |
| 50 | Moderate effect | Crop injury more lasting, recovery | Deficient to moderate weed control |
| 60 |  | Lasting crop injury no recovery | Moderate weed control |
| 70 |  | Heavy injury and stand loss | Control somewhat less than satisfactory |
| 80 | Severe effect | Crop nearly destroyed a few survivors | Satisfactory to good weed control |
| 90 |  | Only occasional live plants left | Very good to excellent control |
| 100 | Completely effective | Complete crop destruction | Complete weed destruction |

A flat for postemergence test was placed in a greenhouse for an 8 to 10 day growing period. The test solution was then hand-sprayed onto the foliage of the emerged test plants. After spraying, the foliage of the test plants was kept dry for 24 hours after which time regular watering was resumed for a period of 13 days. The effect of the test chemical was then recorded in the same manner described for the preemergence tests.

The results of the preemergence and postemergence tests appear in Tables 2 and 3, respectively.

TABLE 2

Preemergence Tests

| Ex. | Barngr PC* or V* K* | | Bermudgr PC or V K | | Bindweed PC or V K | | Corn-F PC or V K | | Greenfox PC or V K | | Johngr PC or V K | |
|---|---|---|---|---|---|---|---|---|---|---|---|---|
| 1 | 3 | 0 | | | 4 | 0 | 4 | 60 | 3 | 0 | 4 | 0 |
| 3 | 0 | 100 | | | 0 | 100 | 2 | 30 | 0 | 100 | 2 | 95 |
| 6 | 0 | 100 | 1 | 60 | 1 | 90 | 1 | 0 | 0 | 100 | 1 | 50 |
| 7 | 0 | 100 | 2 | 50 | 2 | 90 | 1 | 30 | 0 | 100 | 1 | 75 |
| 15 | 0 | 100 | 0 | 100 | 3 | 95 | 0 | 100 | 0 | 100 | 0 | 100 |
| 16 | 0 | 100 | 0 | 100 | 3 | 95 | 2 | 70 | 0 | 100 | 1 | 50 |
| 19 | 0 | 100 | | | 2 | 80 | 0 | 100 | 0 | 100 | 0 | 100 |
| 20 | | | 2 | 90 | | | | | 2 | 0 | | |
| 22 | 0 | 100 | | | 2 | 95 | 0 | 100 | 0 | 100 | 0 | 100 |
| 24 | 2 | 95 | | | 0 | 100 | 0 | 100 | 0 | 100 | 0 | 100 |
| 27 | 0 | 100 | | | 3 | 95 | 0 | 100 | 0 | 100 | 1 | 75 |
| 28 | 0 | 100 | | | 0 | 100 | 0 | 100 | 0 | 100 | 0 | 100 |
| 30 | 0 | 100 | | | 2 | 95 | 1 | 70 | 0 | 100 | 0 | 100 |
| 31 | 0 | 100 | | | 1 | 95 | 2 | 95 | 0 | 100 | 2 | 85 |
| 32 | 0 | 100 | | | 0 | 100 | 0 | 100 | 0 | 100 | 1 | 85 |
| 33 | 0 | 100 | | | 3 | 85 | 0 | 100 | 0 | 100 | 0 | 100 |
| 35 | 0 | 100 | | | 0 | 100 | 0 | 100 | 0 | 100 | 0 | 100 |
| 37 | 100 | | | | 100 | | 100 | | 100 | | 90 | |
| 43 | 0 | 100 | | | 2 | 95 | 0 | 100 | 0 | 100 | 0 | 100 |
| 44 | 0 | 100 | | | 3 | 30 | 2 | 70 | 0 | 100 | 0 | 100 |
| 48 | | | 0 | 100 | 0 | 100 | | | | | 0 | 100 |
| 62 | 0 | 100 | 0 | 100 | 0 | 100 | 2 | 0 | 0 | 100 | 1 | 50 |
| 64 | 0 | 100 | 2 | 40 | 3 | 77 | 2 | 0 | 3 | 95 | 2 | 50 |
| 67 | 0 | 100 | | | 3 | 30 | 0 | 100 | 0 | 100 | 0 | 100 |
| 71 | 95 | | | | 90 | | 80 | | 95 | | 90 | |
| 72 | 30 | | | | 10 | | 0 | | 0 | | 30 | |
| 74 | 100 | | | | 100 | | 90 | | 95 | | 95 | |

| Ex. | Cotton/ Lima Bean PC or V K | | Mrnglory PC or V K | | Yellow Nutsedge PC or V K | | Soybean PC or V K | | Velvetlf PC or V K | | Wheat PC or V K | |
|---|---|---|---|---|---|---|---|---|---|---|---|---|
| 1 | 4 | 0 | 4 | 0 | | 4 | 0 | 4 | 0 | 4 | 0 | |
| 3 | 0 | 100 | 0 | 100 | | | 3 | 0 | 2 | 95 | 0 | 100 |
| 6 | 2 | 40 | 0 | 100 | 2 | | 4 | 0 | 0 | 100 | 0 | 100 |
| 7 | 2 | 50 | 1 | 80 | 3 | 0 | 4 | 0 | 0 | 100 | 0 | 100 |
| 15 | 3 | 0 | 100 | 3 | 30 | 5 | 0 | 0 | 100 | 2 | 90 | |
| 16 | 4 | 0 | 2 | 90 | 2 | 0 | 4 | 0 | 0 | 100 | 2 | 30 |
| 19 | 0 | 100 | 3 | 80 | | | 4 | 0 | 0 | 100 | 0 | 100 |
| 20 | | | | | 1 | 70 | | | | | | |
| 22 | 0 | 100 | 2 | 95 | | | 4 | 0 | 0 | 100 | 0 | 100 |
| 24 | 0 | 100 | 0 | 100 | | | 4 | 0 | 0 | 100 | 0 | 100 |
| 27 | 0 | 100 | 0 | 100 | | | 4 | 0 | 1 | 95 | 0 | 100 |
| 28 | 0 | 100 | 0 | 100 | | | 3 | 0 | 1 | 50 | 0 | 100 |
| 30 | 0 | 100 | 0 | 100 | | | 2 | 0 | 0 | 100 | 0 | 100 |
| 31 | 0 | 100 | 2 | 95 | | | 3 | 0 | 1 | 30 | 0 | 100 |
| 32 | 2 | 95 | 2 | 95 | | | 4 | 0 | 1 | 95 | 0 | 100 |
| 33 | 0 | 100 | 3 | 95 | | | 4 | 0 | 0 | 100 | 0 | 100 |
| 35 | 0 | 100 | 0 | 100 | | | 4 | 0 | 0 | 100 | 0 | 100 |
| 37 | 100 | | 100 | | | | 20 | | 100 | | 100 | |
| 43 | 0 | 100 | 4 | 50 | | | 4 | 0 | 0 | 100 | 0 | 100 |
| 44 | 3 | 0 | 4 | 0 | | | 4 | 0 | 0 | 100 | 2 | 0 |
| 48 | | | | | 1 | 90 | | | | | | |
| 62 | 3 | 0 | 0 | 100 | 2 | 0 | 3 | 0 | 0 | 100 | 2 | 0 |
| 64 | 3 | 20 | 2 | 90 | 4 | 0 | 5 | 0 | 0 | 100 | 0 | 100 |
| 67 | 0 | 100 | 3 | 20 | | | 4 | 0 | 0 | 100 | 2 | 95 |
| 71 | 90 | | 60 | | | | 10 | | 100 | | 100 | |
| 72 | 0 | | 10 | | | | 0 | | 10 | | 0 | |
| 74 | 60 | | 90 | | | | 90 | | 100 | | 95 | |

*K is percent kill; V is a vigor rating and PC is percent control.

TABLE 3

Postemergence Tests

| Ex. | Barngr PC* or V* K* | | Bermudgr PC or V K | | Bindweed PC or V K | | Corn-F PC or V K | | Greenfox PC or V K | | Johngr PC or V K | |
|---|---|---|---|---|---|---|---|---|---|---|---|---|
| 1 | 4 | 0 | | | 4 | 0 | 3 | 0 | 5 | 0 | 4 | 0 |
| 3 | 0 | 100 | | | 4 | 0 | 0 | 100 | 2 | 95 | 0 | 100 |
| 6 | 3 | 0 | | | 3 | 0 | 3 | 0 | 3 | 50 | 3 | 0 |
| 7 | 3 | 0 | | | 3 | 0 | 3 | 0 | 3 | 50 | 3 | 0 |

TABLE 3-continued

Postemergence Tests

| Ex. | | | | | | | | | | | | |
|---|---|---|---|---|---|---|---|---|---|---|---|---|
| 15 | 2 | 0 | | | 3 | 0 | 2 | 0 | 3 | 0 | 3 | 60 |
| 16 | 2 | 0 | 4 | 0 | 3 | 0 | 2 | 0 | 3 | 20 | 3 | 45 |
| 19 | 2 | 95 | | | 4 | 0 | 0 | 100 | 2 | 90 | 0 | 100 |
| 22 | 0 | 100 | | | 2 | 70 | 2 | 65 | 2 | 90 | 0 | 100 |
| 24 | 2 | 25 | | | 3 | 20 | 2 | 0 | 3 | 10 | 2 | 40 |
| 27 | 2 | 30 | | | 3 | 10 | 2 | 65 | 2 | 40 | 2 | 10 |
| 28 | 2 | 0 | | | 2 | 10 | 2 | 0 | 2 | 10 | 2 | 10 |
| 30 | 3 | 0 | | | 3 | 0 | 2 | 0 | 2 | 0 | 2 | 20 |
| 31 | 2 | 30 | | | 2 | 20 | 2 | 35 | 2 | 30 | 2 | 80 |
| 32 | 3 | 10 | | | 4 | 0 | 2 | 0 | 3 | 0 | 2 | 10 |
| 33 | 2 | 0 | | | 3 | 0 | 2 | 0 | 2 | 0 | 2 | 30 |
| 35 | 0 | 100 | | | 0 | 100 | 2 | 0 | 0 | 100 | 0 | 100 |
| 37 | 40 | | | | 50 | | 30 | | 60 | | 60 | |
| 43 | 2 | 60 | | | 4 | 0 | 2 | –0 | 3 | 0 | 0 | 100 |
| 44 | 2 | 90 | | | 4 | 0 | 2 | 0 | 3 | 30 | 0 | 100 |
| 62 | 4 | 0 | | | 5 | 0 | 3 | 0 | 4 | 0 | 4 | 0 |
| 64 | 3 | 0 | 5 | 0 | 3 | 0 | 3 | 0 | 3 | 90 | 3 | 0 |
| 67 | 2 | 95 | | | 3 | 0 | 0 | 100 | 2 | 95 | 0 | 100 |
| 71 | 95 | | | | 90 | | 90 | | 100 | | 95 | |
| 72 | 30 | | | | 30 | | 20 | | 0 | | 30 | |
| 74 | 95 | | | | 40 | | 80 | | 100 | | 95 | |

Plant

| Ex. | Cotton/Lima Bean PC or | | Mrnglory PC or | | Yellow Nutsedge PC or | | Soybean PC or | | Velvetlf PC or | | Wheat PC or | |
|---|---|---|---|---|---|---|---|---|---|---|---|---|
| | V | K | V | K | V | K | V | K | V | K | V | K |
| 1 | 4 | 0 | 4 | 0 | | | 5 | 0 | 2 | 0 | 4 | 0 |
| 3 | 4 | 10 | 3 | 0 | | | 3 | 0 | 2 | 30 | 0 | 100 |
| 6 | 3 | 0 | 3 | 0 | | | 4 | 0 | 3 | 0 | 3 | 0 |
| 7 | 3 | 0 | 3 | 0 | | | 4 | 0 | 2 | 0 | 3 | 0 |
| 15 | 3 | 0 | 3 | 0 | | | 4 | 0 | 3 | 30 | 3 | 0 |
| 16 | 3 | 0 | 4 | 0 | 5 | 0 | 4 | 0 | 3 | 30 | 3 | 0 |
| 19 | 3 | 0 | 4 | 0 | | | 3 | 0 | 2 | 40 | 0 | 100 |
| 22 | 3 | 0 | 4 | 0 | | | 4 | 0 | 0 | 100 | 2 | 90 |
| 24 | 4 | 0 | 4 | 0 | | | 4 | 0 | 2 | 50 | 2 | 30 |
| 27 | 4 | 0 | 4 | 0 | | | 4 | 0 | 0 | 100 | 2 | 40 |
| 28 | 4 | 0 | 4 | 0 | | | 4 | 0 | 2 | 60 | 2 | 60 |
| 30 | 3 | 0 | 4 | 0 | | | 4 | 0 | 0 | 100 | 2 | 0 |
| 31 | 3 | 0 | 4 | 0 | | | 4 | 0 | 2 | 20 | 2 | 60 |
| 32 | 4 | 0 | 4 | 0 | | | 4 | 0 | 3 | 30 | 2 | 20 |
| 33 | 3 | 0 | 3 | 0 | | | 4 | 0 | 0 | 100 | 2 | 0 |
| 35 | 2 | 90 | 0 | 100 | | | 3 | 0 | 0 | 100 | 0 | 100 |
| 37 | 20 | | 20 | | | | 20 | | 40 | | 40 | |
| 43 | 3 | 0 | 4 | 0 | | | 4 | 0 | 3 | 0 | 2 | 60 |
| 44 | 3 | 0 | 4 | 0 | | | 4 | 0 | 2 | 30 | 0 | 100 |
| 62 | 3 | 0 | 4 | 0 | | | 4 | 0 | 4 | 0 | 5 | 0 |
| 64 | 3 | 0 | 4 | 0 | 5 | 0 | 4 | 0 | 2 | 0 | 3 | 0 |
| 67 | 3 | 0 | 4 | 0 | | | 3 | 0 | 3 | 0 | 0 | 100 |
| 71 | 70 | | 50 | | | | 40 | | 60 | | 80 | |
| 72 | 0 | | 10 | | | | 50 | | 40 | | 0 | |
| 74 | 40 | | 40 | | | | 60 | | 40 | | 70 | |

*K is percent kill; V is a vigor rating and PC is percent control.

What is claimed is:

1. A herbicidal isoxazolidinone of the formula

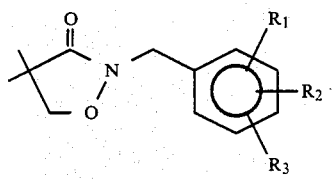

or an agriculturally acceptable salt thereof in which $R_1$ and $R_2$ are independently selected from -hydrogen and -halogen; and $R_3$ is of the formula

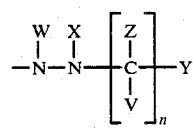

wherein
n is 0 or 1, and
when n is 0
W is selected from -hydrogen, one to six carbon alkyl, one to six carbon haloalkanoyl, and -benzoyl;
X is selected from -hydrogen and one to six carbon alkyl; and
Y is selected from -hydrogen, one to six carbon alkyl, three to eight carbon -cycloalkyl, one to six carbon alkanoyl, one to six carbon haloalkanoyl, -benzoyl, -2-nitro-5-(2-chloro-4-trifluoromethylphenoxy)-benzoyl, -2,4-dichlorophenoxyacetyl, one to six carbon alkyloxy-carbonyl, one to six carbon alkylaminocarbonyl, -phenylaminocarbonyl, and one to six carbon alkylthiocarbonyl, provided that when Y and W are both haloalkanoyl or benzoyl groups, Y is the same as W; or W and X together constitute a chemical bond; and Y is selected from $\equiv$N and one to six carbon alkyloxycarbonyl; and when n is 1, X and Z together constitute a chemical bond;

W is -hydrogen;

V is selected from -hydrogen and one to six carbon alkyl; and

Y is selected from one to six carbon alkyl, -phenyl, -carboxyl, and one to six carbon alkyloxycarbonyl, or V and Y together are an alkyl chain of 4–6 carbon atoms.

2. A compound of claim 1 wherein $R_1$ is 2-chloro and $R_2$ is hydrogen.

3. A compound of claim 1 wherein W is hydrogen.

4. 2-[(2-Chloro-6-hydrazinophenyl)methyl]-4,4-dimethyl-3-isoxazolidinone, a compound of claim 1.

5. 2-[(2-Chloro-4-hydrazinophenyl)methyl]-4,4-dimethyl-3-isoxazolidinone, a compound of claim 1.

6. 2-[(2-Chloro-4-hydrazinophenyl)methyl]-4,4-dimethyl-3-isoxazolidinone hydrochloride, a compound of claim 1.

7. 2-[(2-Chloro-5-hydrazinophenyl)methyl]-4,4-dimethyl-3-isoxazolidinone, a compound of claim 1.

8. 2-[(2-Chloro-5-hydrazinophenyl)methyl]-4,4-dimethyl-3-isoxazolidinone hydrochloride, a compound of claim 1.

9. 2-[[2-Chloro-4-[(1-methylethyl)carbonylhydrazo]phenyl]methyl]-4,4-dimethyl-3-isoxazolidinone, a compound of claim 1.

10. 2-[[2-Chloro-4-2-nitro-5-(2-chloro-4-trifluoromethylphenoxy)phenylcarbonylhydrazo]phenyl]methyl]-4,4-dimethyl-3-isoxazolidinone, a compound of claim 1.

11. 2-[[2-Chloro-4-(2-ethylidenyl-1-hydrazinyl)phenyl]methyl]-4,4-dimethyl-3-isoxazolidinone, a compound of claim 1.

12. 2-[[2-Chloro-4-(2-propylidenyl-1-hydrazinyl)phenyl]methyl]-4,4-dimethyl-3-isoxazolidinone, a compound of claim 1.

13. 2-[[2-Chloro-4-[2-(1-methylethylidenyl)-1-hydrazinyl]phenyl]methyl]-4,4-dimethyl-3-isoxazolidinone, a compound of claim 1.

14. 2-[[2,4-Dichloro-5-[2-(1-methylethylidenyl)-1-hydrazinyl]phenyl]methyl]-4,4-dimethyl-3-isoxazolidinone, a compound of claim 1.

15. 2-[[2-Chloro-6-(2-cyclohexylidenyl-1-hydrazinyl)phenyl]methyl]-4,4-dimethyl-3-isoxazolidinone, a compound of claim 1.

16. 2-[[2-Chloro-4-(2-cyclohexylidenyl-1-hydrazinyl)phenyl]methyl]-4,4-dimethyl-3-isoxazolidinone, a compound of claim 1.

17. A herbicidal composition comprising a herbicidally effective amount of at least one compound of claim 1 in admixture with agriculturally acceptable adjuvants, carriers, diluents, or complementary pesticides.

18. A method for controlling the growth of plants which comprises applying to the locus where control is desired a herbicidally effective amount of at least one compound of claim 1.

* * * * *

UNITED STATES PATENT AND TRADEMARK OFFICE
CERTIFICATE OF CORRECTION

PATENT NO. : 4,692,182

DATED : September 8, 1987

INVENTOR(S) : Jun H. Chang

It is certified that error appears in the above-identified patent and that said Letters Patent is hereby corrected as shown below:

In the ABSTRACT, line 11 after the second formula, "nvl, - lower alkyloxycarbonyl, -lower alkylaminocar-", should read --nvl, -lower alkylaminocar--. Column 1, line 29, "and $R_2$ independently" should read --and $R_2$ are independently--. Column 3, line 34, "was obtained by treating of the" should read --was obtained by treatment of the --; Column 3, line 48, "in acetonitrile 25 ml)" should read --in acetonitrile (25 ml)--. Column 10, line 7, "pitted morningingglory" should read --pitted morning glory--. Column 11, Table 2, Example 20, first occurrence, under heading "Bindweed PC or V K", --3 90-- should appear; under heading "Johngr PC or V K", --2 0-- should appear. Example 1, second occurrence, under heading "Yellow Nutsedge PC or V K", delete "4"; under heading "Soybean PC or V K", "0 4" should read --4 0--; under heading "Velvetlf PC or V K", "0 4" should read --4 0--; under heading "Wheat PC or V K", "0" should read --4 0--. Example 15, second occurrence should read --
3 0  0 100  3 30  5 0  0 100  2 90--. Column 14, line 68, "carbon alkyloxy-carbonyl," should read --carbon alkyloxycarbonyl,--. Column 16, line 4, Claim 10, "2-[[2-Chloro-4-2-nitro" should read "2-[[2-Chloro-4-[2-nitro--.

Signed and Sealed this

Fifteenth Day of March, 1988

Attest:

DONALD J. QUIGG

Attesting Officer

Commissioner of Patents and Trademarks